United States Patent [19]
Seto

[11] Patent Number: 5,151,755
[45] Date of Patent: Sep. 29, 1992

[54] METHOD FOR DETECTING DEFECTS IN MEASUREMENT MEANS OF BIOCHEMICAL ANALYSIS APPARATUSES

[75] Inventor: Shunichi Seto, Kanagawa, Japan
[73] Assignee: Fuji Photo Film Co., Ltd., Kanagawa, Japan
[21] Appl. No.: 567,569
[22] Filed: Aug. 16, 1990
[30] Foreign Application Priority Data Aug. 16, 1989 [JP] Japan .................................. 1-211085

[51] Int. Cl.$^5$ ............................................. G01N 21/25
[52] U.S. Cl. ..................................... 356/414; 356/418
[58] Field of Search ............... 356/414, 446, 236, 416, 356/418, 419, 425, 243, 237; 250/252.1 A; 422/82.05

[56] References Cited

U.S. PATENT DOCUMENTS

| 3,526,480 | 9/1970 | Findl et al. |
| 3,874,799 | 4/1975 | Isaacs et al. .................. 356/236 |
| 3,992,158 | 11/1976 | Przybylowica et al. |
| 4,040,747 | 8/1977 | Webster ........................ 356/446 |
| 4,292,272 | 9/1981 | Kitajima et al. |
| 4,830,503 | 5/1989 | Hoda et al. ................... 356/446 |

Primary Examiner—F. L. Evans
Assistant Examiner—K. P. Hantis
Attorney, Agent, or Firm—Sughrue, Mion, Zinn Macpeak & Seas

[57] ABSTRACT

Defects in a measurement device are detected in a biochemical analysis apparatus wherein a droplet of liquid sample is applied to an analysis medium containing a reagent, which chemically reacts with a specific constituent in the liquid sample, the analysis medium is then incubated, the optical densities of the analysis medium are determined, and concentration of the specific constituent in the liquid sample is determined from the optical densities of the analysis media thus determined. The method for detecting defects comprises the steps of irradiating light, which has passed through a plurality of interference filters by turns, to a reference density plate, and measuring the amount of light reflected by the reference density plate. Measured values representing the amounts of reflected light, which have thus been measured for the interference filters, are compared with one another. Defects in the measurement device are detected from the results of the comparison.

13 Claims, 9 Drawing Sheets

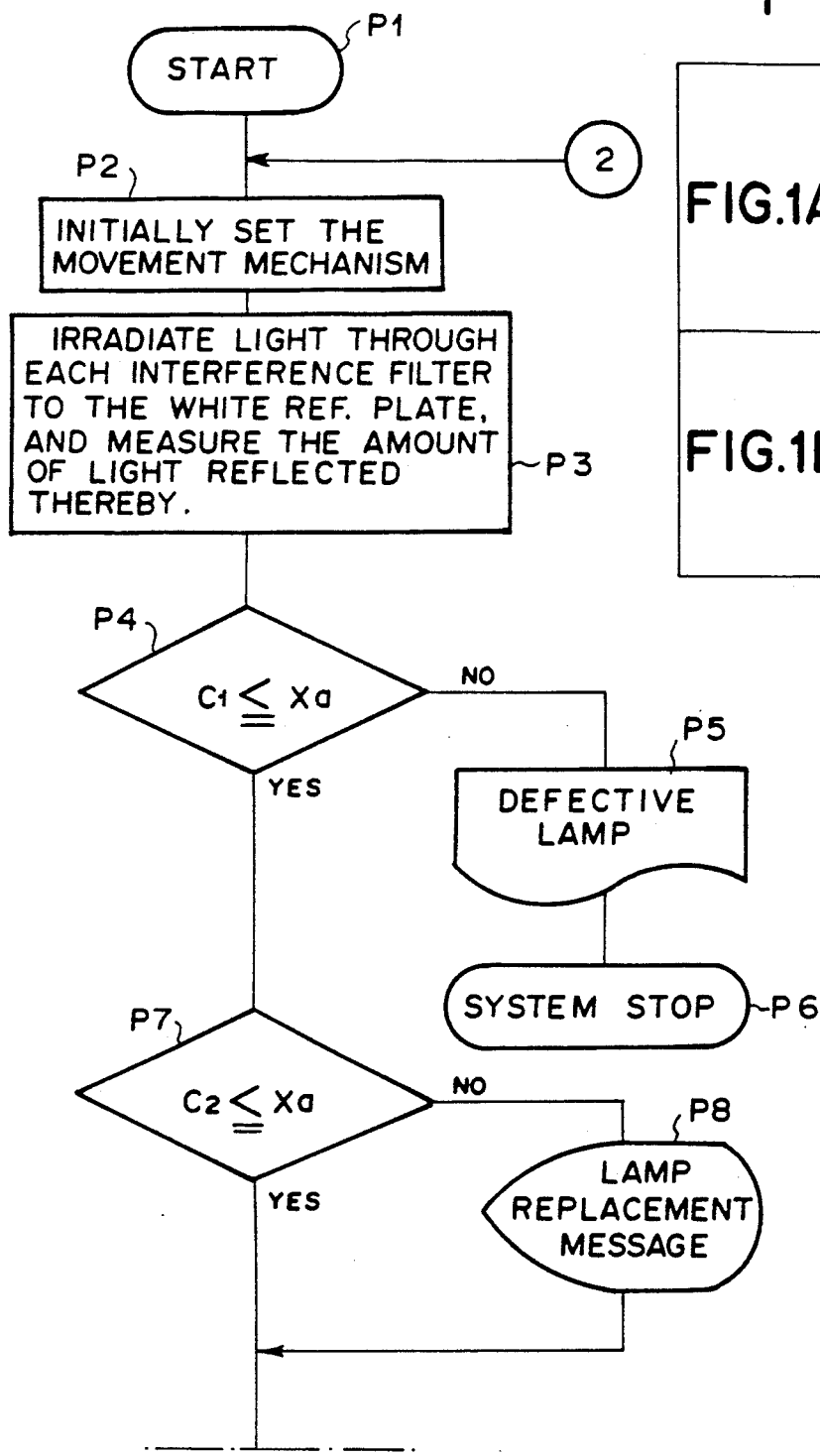

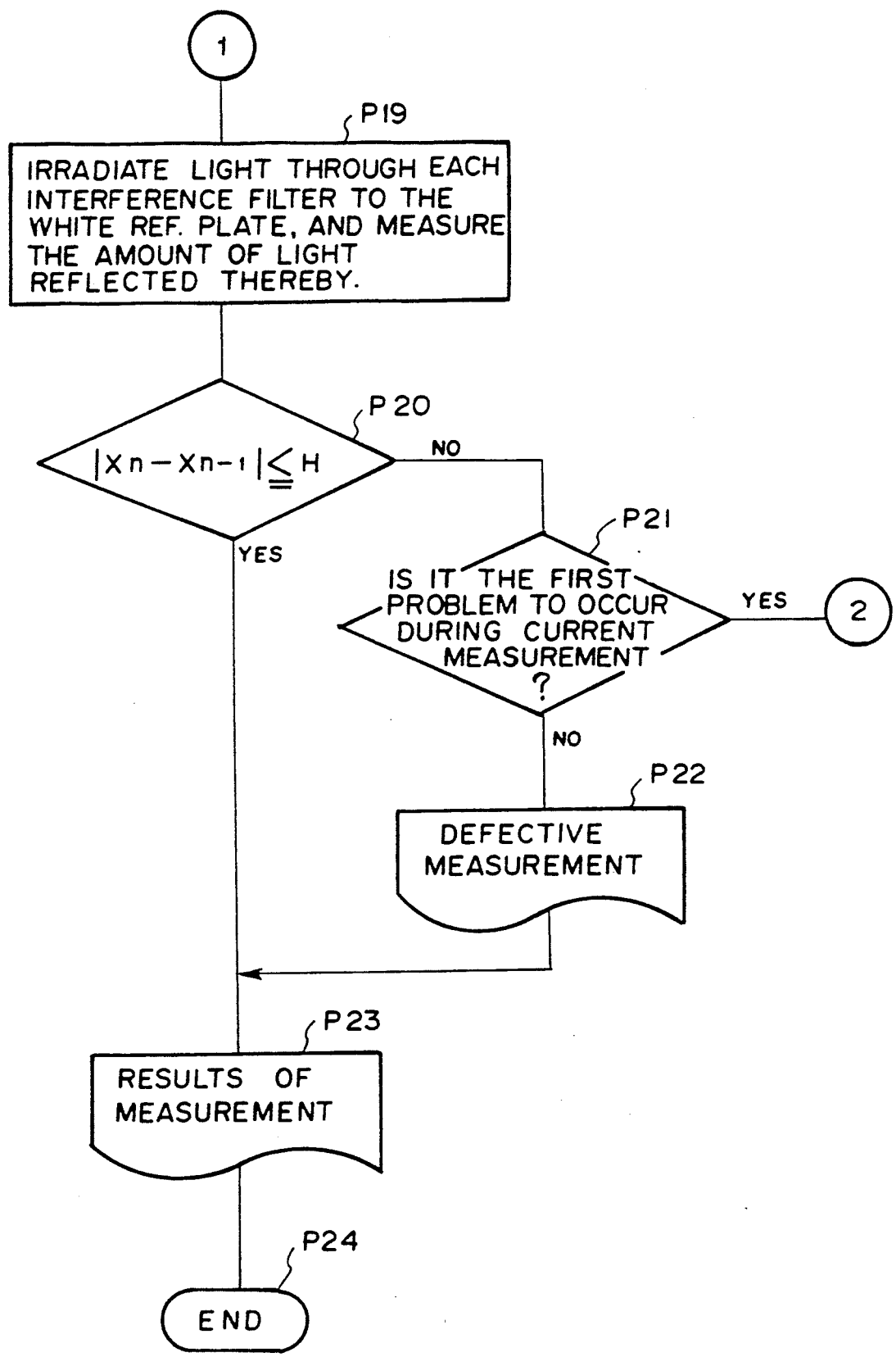

F I G. 2
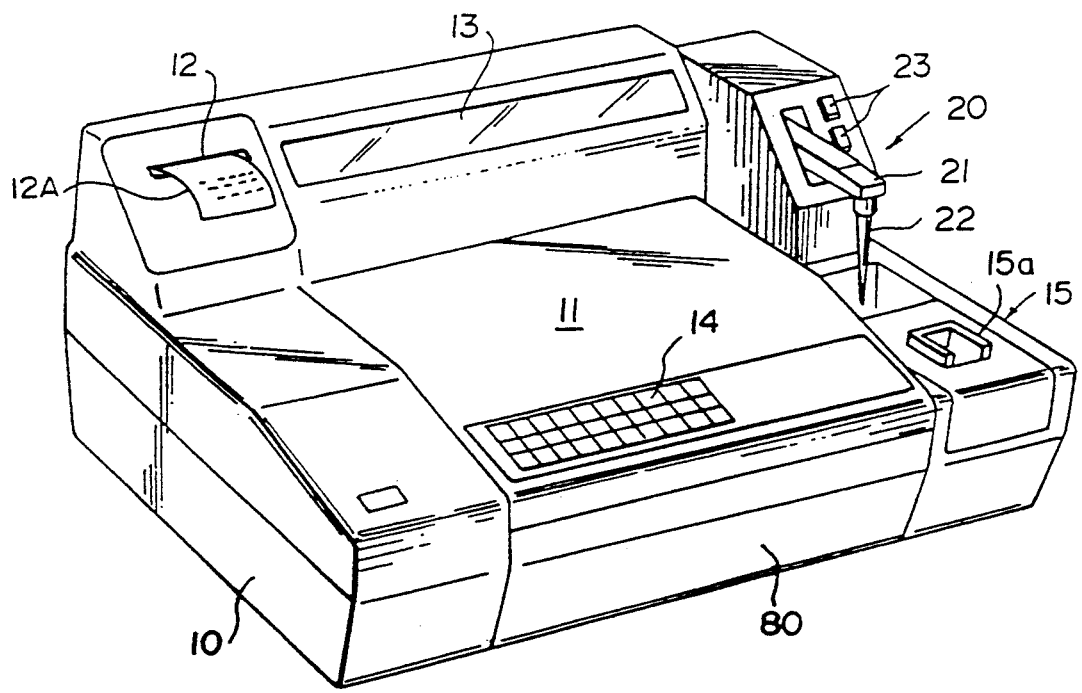

METHOD FOR DETECTING DEFECTS IN MEASUREMENT MEANS OF BIOCHEMICAL ANALYSIS APPARATUSES

BACKGROUND OF THE INVENTION

1. Field of the Invention

This invention relates to a method for detecting defects in a measurement means of a biochemical analysis apparatus, with which specific constitutuents in liquid samples are analyzed chemically. This invention particularly relates to a method for detecting defects in a measurement means of a biochemical analysis apparatus wherein a droplet of liquid sample is applied to an analysis medium, such as a chemical analysis slide or test film, containing a reagent which reacts with the liquid sample, and the optical density, which depends on how much of a reaction product was formed by the reaction between each liquid sample and the reagent in each analysis medium, is found.

2. Description of the Prior Art

Qualitative or quantitative analyses of specific chemical constituents in liquid samples are conducted for various industrial purposes. Particularly, it is very important in biochemical and clinical fields to be able to quantitatively analyze certain chemical or physical constituents in body fluids such as blood or urine.

Recently, as disclosed in, for example, U.S. Pat. Nos. 3,992,158 and 4,292,272, dry type chemical analysis slides were developed for use in systems designed for performing quantitative analysis, with which systems the concentrations of specific chemical constituents or specific physical constituents contained in a droplet of liquid sample, which is applied to the chemical analysis slide, are determined. It is possible to analyze a liquid sample more simply and more quickly with methods in which chemical analysis slides are used than with methods in which conventional wet type analyses are carried out. Therefore, it is more desirable to use chemical analysis slides, particularly in medical organizations, research laboratories, or the like, where many samples must be analyzed, than to carry out conventional wet type analyses.

In order for a chemical analysis slide to be used in the determination of the concentration of a specific constituent contained in a liquid sample, a measured amount of the liquid sample is put on the chemical analysis slide and is kept at a predetermined temperature (i.e. incubated) for a predetermined time in an incubator, which causes a color reaction. The chemical analysis slide is then exposed to light having a wavelength which is selected in advance. The selection of the wavelength depends on the kind of the chemical analysis slide (or the constituents of the liquid sample and the constituents of a reagent contained in the reagent layer in the chemical analysis slide). Light is thus irradiated to a reaction product which forms on the chemical analysis slide, and the amount of light reflected by the reaction product is measured. The optical density of the chemical analysis slide is then found from the measured amount of reflected light.

Also, as a means with which liquid samples can be automatically and sequentially analyzed, a novel apparatus is proposed in, for example, U.S. Pat. No. 3,526,480. In the proposed apparatus, a long tape-like test film containing a reagent is used instead of the aforesaid chemical analysis slides, and the application, incubation and measurement of samples are carried out sequentially on adjacent portions of the test film.

In general, in the biochemical analysis apparatuses utilizing the analysis media, such as chemical analysis slides or test films, many kinds of analysis media are used depending on what the specific constituent to be analyzed is. In such cases, light having different wavelengths should be prepared depending on the kind of the analysis medium, i.e. what the specific constituent to be analyzed is. In many cases, for this purpose, only a single light source is used, and light produced by the light source is selectively passed through one of a plurality of interference filters. In this manner, light having different wavelengths can be obtained.

The accuracy of the biochemical analysis utilizing the analysis media, such as chemical analysis slides or test films, is adversely affected by defects in the measurement means of the biochemical analysis apparatus. The defects in the measurement means include a change in the amount of light produced by a light source (lamp) due to deterioration of the light source with the passage of time, and a change in the absorbance or the transmission characteristics due to deterioration of interference filters with the passage of time. The defects also include a deviation in position of a probe, a filter wheel, or the light source.

SUMMARY OF THE INVENTION

The primary object of the present invention is to provide a method for detecting defects in a measurement means of a biochemical analysis apparatus, with which defects in a measurement means, such as deterioration of interference filters, deterioration of a light source, and deviation in position of elements of the measurement means, are detected easily without any particular apparatus being used.

Another object of the present invention is to provide a method for detecting defects in a measurement means of a biochemical analysis apparatus, which makes the biochemical analysis apparatus reliable.

The present invention provides a method for detecting defects in a measurement means of a biochemical analysis apparatus wherein a droplet of liquid sample is applied to an analysis medium containing a reagent, which chemically reacts with a specific constituent in the liquid sample, the analysis medium is then incubated, the optical densities of the analysis medium are determined, and concentrations of the specific constituent in the liquid sample are determined from the optical densities of the analysis medium thus determined, the method for detecting defects in a measurement means of a biochemical analysis apparatus comprising the steps of:
i) irradiating light, which has passed through a plurality of interference filters by turns, to a reference density plate at predetermined time intervals, to measure the amount of light reflected by said reference density plate,
ii) comparing a set of measured values representing the amounts of reflected light, which have thus been measured, with one another, and
iii) detecting defects in the measurement means from the results of the comparison.

When the same amount of light is irradiated to a black reference plate and a white reference plate, which serve as reference density plates, the amount of light reflected by a black reference plate is markedly smaller than the amount of light reflected by a white reference plate.

Also, in cases where a black reference plate is employed as the reference density plate, the amount of light reflected by the black reference plate does not largely vary between when light, which has passed through a normal interference filter, is irradiated to the black reference plate and when light, which has passed through a deteriorated interference filter, is irradiated to the black reference plate. Therefore, a white reference plate should preferably be employed as the reference density plate.

In general, the probability that a plurality of interference filters will deteriorate approximately simultaneously is very low. Particularly, in cases where several or more interference filters are provided as in most of biochemical analysis apparatuses, it is not thought that all of the interference filters will deteriorate approximately simultaneously. Therefore, deteriorated interference filters can be detected by comparing the measured values representing the amounts of reflected light, which have been measured in the manner described above, with one another. Specifically, by way of example, measured values $Xa$, $Xb$, and $Xc$ are obtained for interference filters a, b, and c. In cases where the value of $Xb/Xa$ differs markedly from the value obtained when the respective interference filters are normal, which can be calculated in advance, and the value of $Xc/Xa$ is close to the value obtained when the respective interference filters are normal, it can be regarded that the measured value $Xb$ is abnormal, i.e. the interference filter b has been deteriorated. In cases where both the value of $Xb/Xa$ and the value of $Xc/Xa$ differ markedly from the values obtained when the respective interference filters are normal, it can be regarded that the measured value $Xa$ is abnormal, i.e. the interference filter a has been deteriorated.

As described above, with the method for detecting defects in a measurement means of a biochemical analysis apparatus in accordance with the present invention, light, which has passed through one of a plurality of interference filters, is irradiated to a reference density plate, and the amount of light reflected by the reference density plate is measured. The irradiation of light to the reference density plate and the measurement of the amount of light reflected by the reference density plate are repeated for all of the plurality of interference filters. The measured values representing the amounts of reflected light, which have thus been measured, are then compared with one another. Therefore, defects in the measurement means, such as deterioration of the interference filters, deterioration of the light source, and deviation in position of elements of the measurement means, can be detected easily and accurately. Accordingly, with the method for detecting defects in a measurement means of a biochemical analysis apparatus in accordance with the present invention, the problem can be prevented from occurring in that light having inappropriate wavelengths is used during the finding of the optical densities of analysis media. As a result, the reliability of the biochemical analysis apparatus can be kept high.

BRIEF DESCRIPTION OF THE DRAWINGS

FIG. 2 is a perspective view showing an example of a biochemical analysis apparatus wherein the embodiment of the method for detecting defects in a measurement means of a biochemical analysis apparatus in accordance with the present invention is employed.

DESCRIPTION OF THE PREFERRED EMBODIMENTS

Figure 1B:
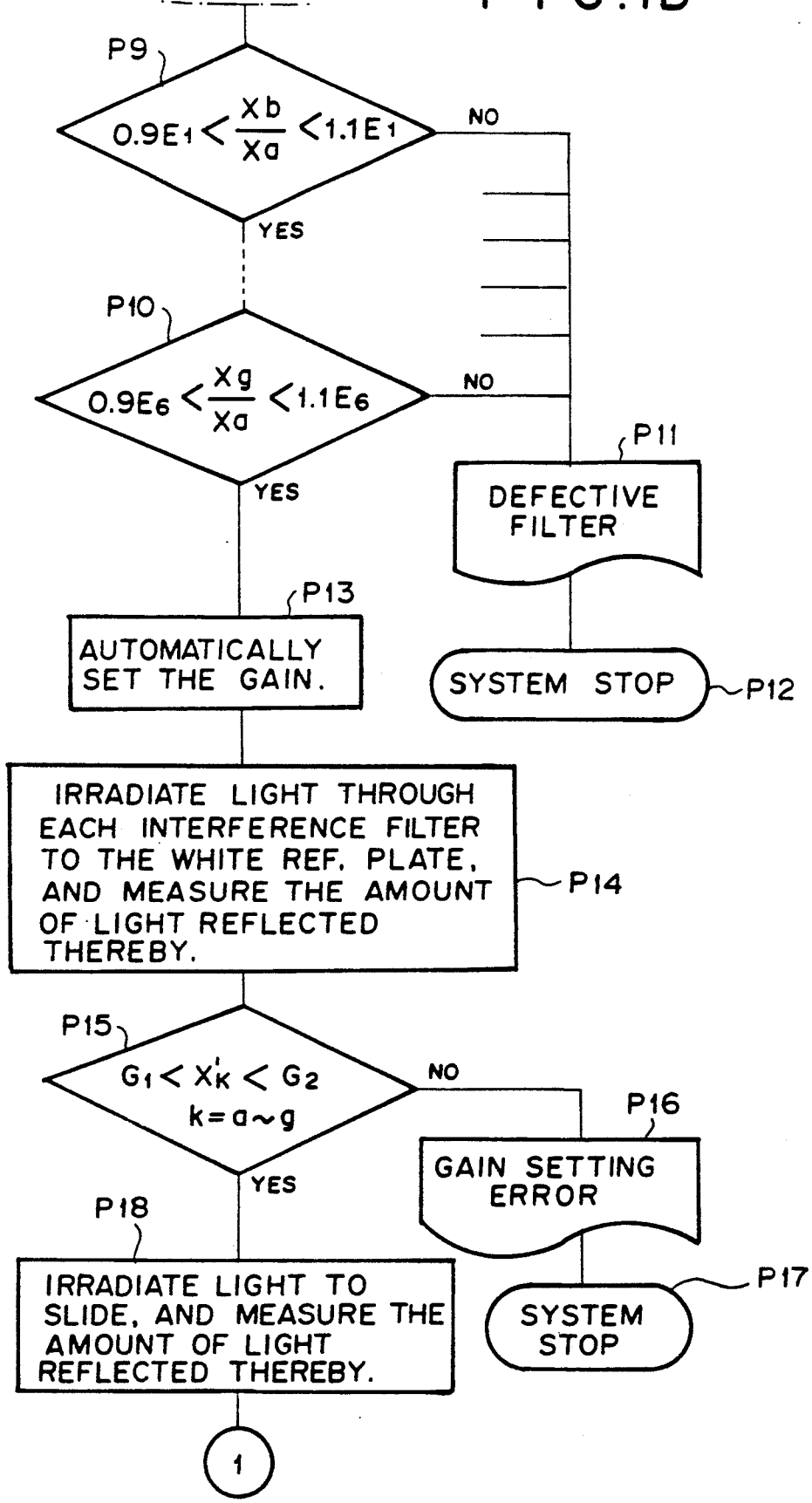
FIG. 1 consisting of FIGS. 1a, 1b and 1c is a flow chart showing how information about measured values representing the amounts of light reflected by a reference density plate is processed in an embodiment of the method for detecting defects in a measurement means of a biochemical analysis apparatus in accordance with the present invention.

The present invention will hereinbelow be described in further detail with reference to the accompanying drawings.

FIG. 2 is a perspective view showing an example of a biochemical analysis apparatus wherein an embodiment of the method for detecting defects in a measurement means of a biochemical analysis apparatus in accordance with the present invention is employed.

With reference to FIG. 2, an incubator, a slide conveyance means, a slide feed-in means, and the like, are disposed in a main body 10, and covered with a cover 11. A display section 13 for displaying the measured values, or the like, a feed-out opening 12 for a sheet 12A on which the displayed information is printed, and an operating key section 14 for controlling the displaying, or the like, are located on the outer side of the chemical analysis apparatus. A slide guide 15a for holding unused chemical analysis slides is located at a slide stand-by section 15 on the right side of the chemical analysis apparatus. A plurality of unused chemical analysis slides are held in the stacked form by the slide guide 15a. Alternatively, a cartridge housing a plurality of chemical analysis slides may be fitted to the slide guide 15a. A sample application means 20 for applying a predetermined liquid sample onto a reagent layer of a chemical analysis slide is located at the rear of the slide stand-by section 15. The sample application means 20 is composed of a sample application arm 21, which projects forwardly and which can rotate vertically around its rear edge, a sample application pipette 22 extending downward from the front end of the sample application arm 21, and operating pushbuttons 23, 23 for controlling the vertical movement of the sample application arm 21 and the drawing-in and discharging of the liquid sample in the sample application pipette 22. In the course of sample application by the sample application means 20, the sample application arm 21 is rotated up to move the sample application pipette 22 up by the operation of the operating buttons 23, 23. The lower edge of the sample application pipette 22 is then dipped in a liquid sample contained in a vessel, and a predetermined amount of the liquid sample is drawn into the sample application pipette 22. Then, the sample application arm 21 is rotated down, and the predetermined amount of the liquid sample is applied from the sample application pipette 22 onto the reagent layer of a chemical analysis slide, which is located below the sample application pipette 22.

Figure 3:
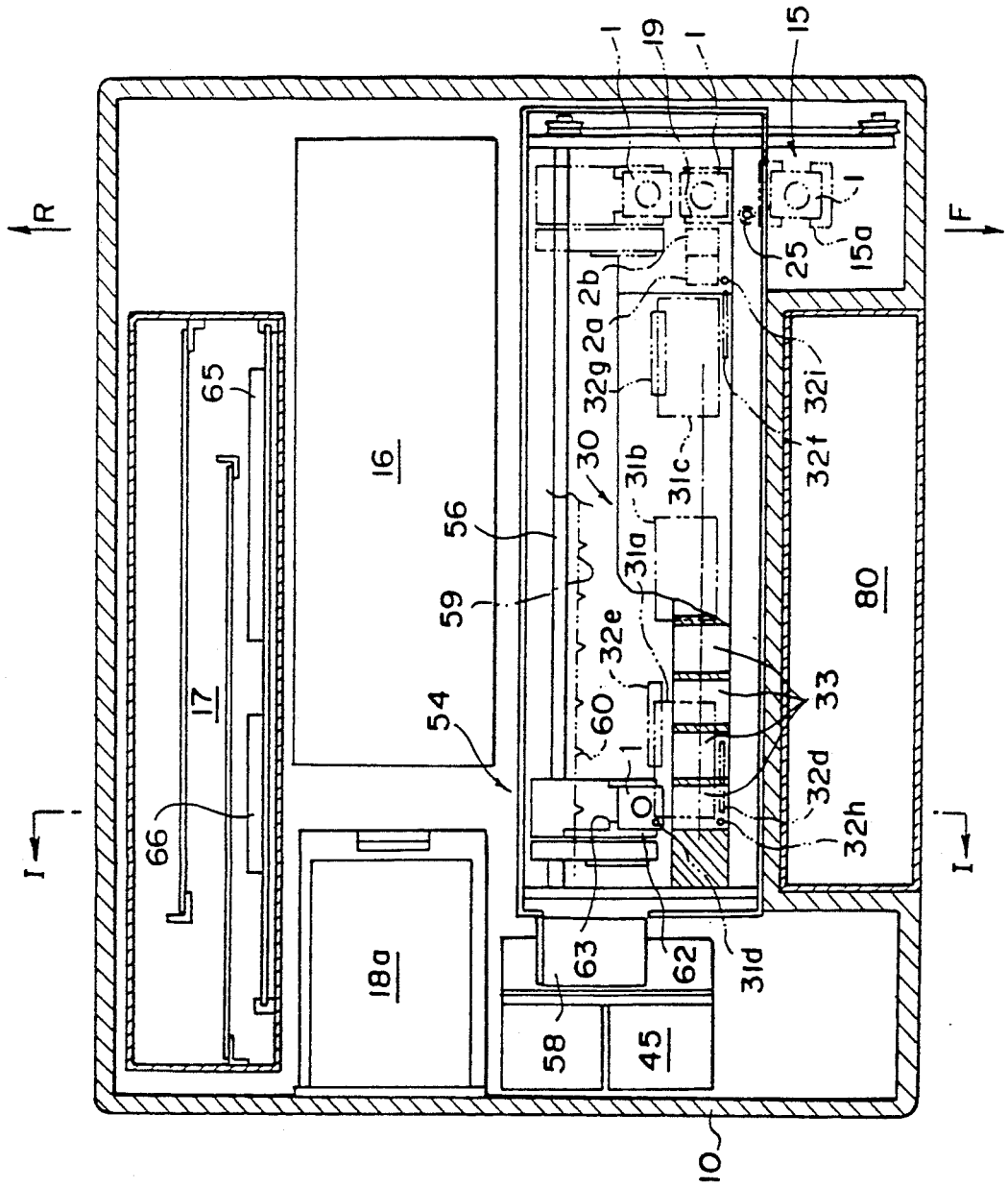
FIG. 3 is a plan view showing the major part of the biochemical analysis apparatus shown in FIG. 2, with a cover thereof being omitted.
Figure 4:
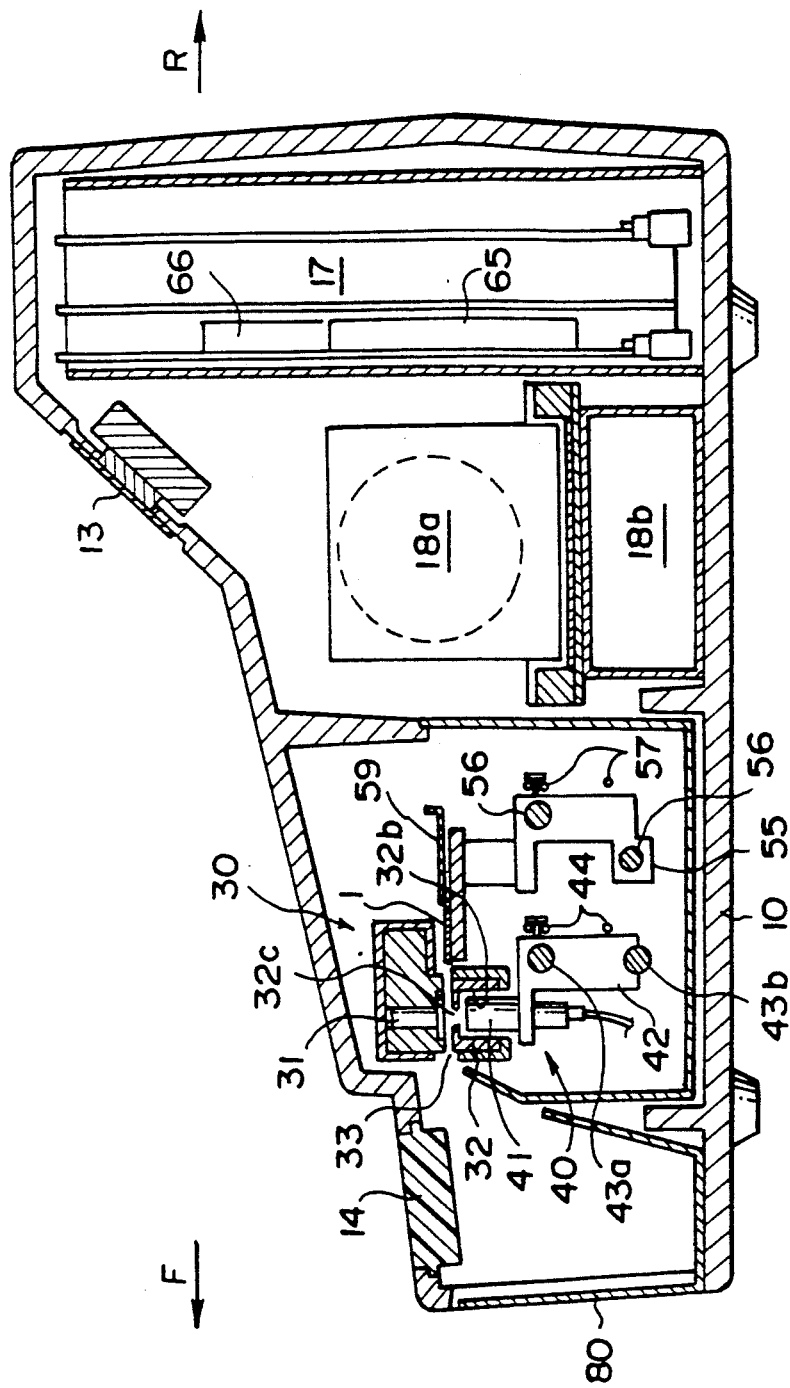
FIG. 4 is a sectional view taken along line I—I of FIG. 3.

FIG. 3 is a plan view showing the major part of the biochemical analysis apparatus shown in FIG. 2, with a cover thereof being omitted. FIG. 4 is a sectional view taken along line I—I of FIG. 3. The internal configuration of the chemical analysis apparatus will hereinbelow be described with reference to FIGS. 3 and 4.

An incubator 30 for incubating a chemical analysis slide 1, to which a liquid sample has been applied by the sample application means 20, is located inside of the biochemical analysis apparatus. Also, a measurement means 40 for finding the extent of a color reaction occurring in a chemical analysis slide 1, which has been incubated, i.e. the reflection density of the chemical analysis slide 1, which has been incubated, is located inside of the biochemical analysis apparatus. Further, a slide conveyance means, which conveys chemical analysis slides 1, 1, . . . from the slide stand-by section 15 to compartments 33, 33, . . . of the incubator 30 is located inside of the chemical analysis apparatus. The slide conveyance means will later be described in detail with reference to FIG. 6. The chemical analysis apparatus is also provided with an electric power source 16, a printed circuit board 17 for a control circuit, a light source 18a for the measurement means 40, and a magnetic disk drive mechanism 18b. In the description below, the direction indicated by the arrow F is referred to as the forward direction or the front side, and the direction indicated by the arrow R is referred to as the backward direction or the rear side. Also, the right side and the left side are referred to with respect to FIG. 3.

The incubator 30 extends in the transverse (i.e. rightward-leftward) direction, and a plurality of the compartments 33, 33, . . . are located side by side in the transverse direction in the incubator 30. The compartments 33, 33, . . . are provided with inlet openings and outlet openings. The inlet openings are located side by side in the transverse direction on the rear side of the compartments 33, 33, . . . The outlet openings are located side by side in the transverse direction on the front side of the compartments 33, 33, . . . A chemical analysis slide 1 is fed into a compartment 33 from its inlet opening, and ejected from its outlet opening. The chemical analysis slide 1, which has been ejected from the outlet opening, is discharged into an ejection box 80, which is located in front of the incubator 30. Also, the compartments 33 are provided with a lower member 32 for supporting the chemical analysis slides 1, 1, . . . thereon, and an upper member 31 for holding the chemical analysis slides 1, 1, . . . which are supported on the lower member 32, from above. The chemical analysis slides 1, 1, . . . are incubated by the upper member 31 and the lower member 32.

The lower member 32 defines a long groove 32b, which extends in the transverse direction and which accommodates a probe 41 for finding the reflection densities of chemical analysis slides 1, 1, . . . accommodated in the compartments 33, 33, . . . The lower member 32 is also provided with openings 32c, 32c, . . . through which the probe 41 irradiate light to the chemical analysis slides 1, 1, . . . during the finding of the reflection densities.

Figure 7:
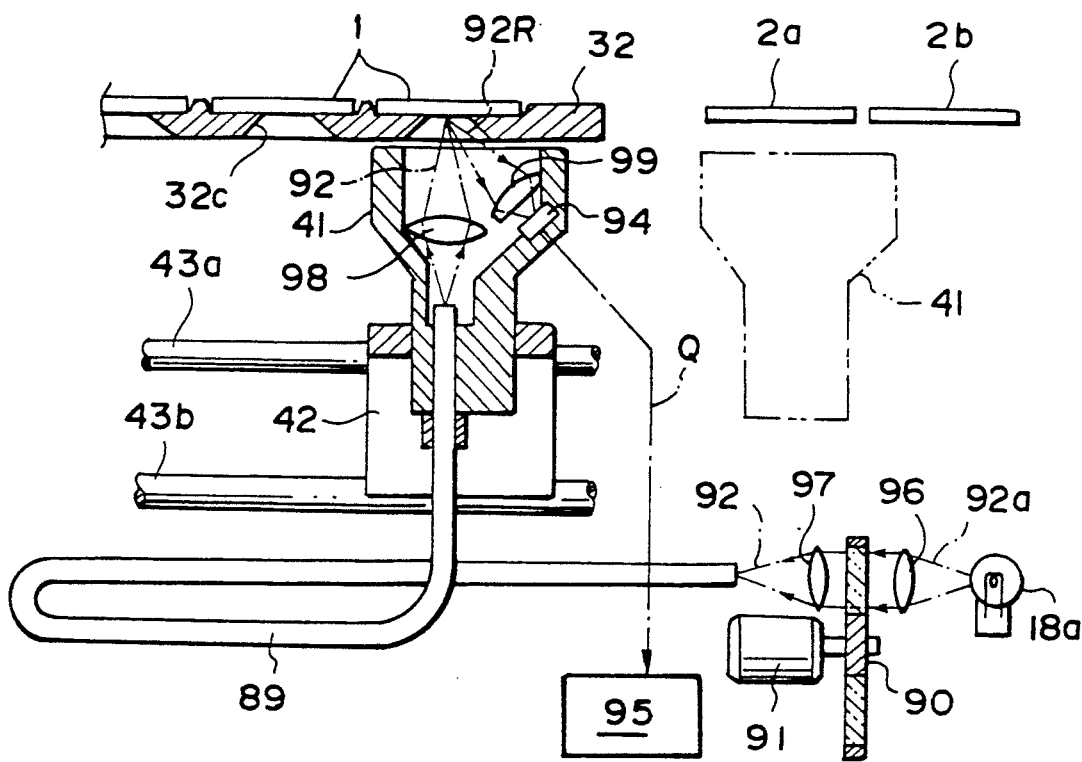
FIG. 7 is a schematic front view showing a probe and surrounding parts of the biochemical analysis apparatus shown in FIG. 2.
Figure 8:
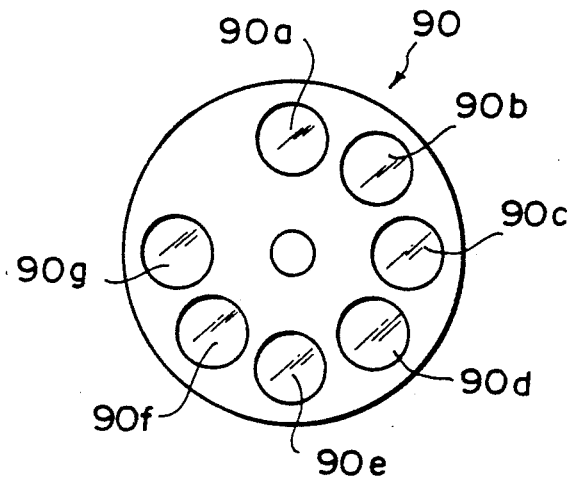
FIG. 8 is a plan view showing a filter plate of the probe.

The probe 41 is supported on a supporting base 42. A wire 44 is connected to the supporting base 42 and is pulled by a motor 45. In this manner, the supporting base 42 is moved in the long groove 32b in the transverse direction by being guided by guide rods 43a and 43b. The probe 41 moves together with the supporting base and finds the reflection density of each chemical analysis slide 1, which is accommodated in each compartment 33. The probe 41 will hereinbelow be described in detail with reference to FIG. 7. One edge of an optical fiber 89 is connected to the probe 41. The other edge of the optical fiber 89 is secured at the position facing the light source 18a. The light source 18a produces light 92a. The light 92a is collimated by a collimator lens 96, and the collimated light passes through a filter plate 90. Light 92, which has passed through the filter plate 90, is then condensed by a condensing lens 97 and impinges upon the other edge of the optical fiber 89. By way of example, as shown in FIG. 8, the filter plate 90 is provided with interference filters 90a, 90b, 90c, 90d, 90e, 90f, and 90g. The filter plate 90 is rotated by a pulse motor 91, and one of the interference filters 90a through 90g is selectively located in the optical path of the light 92a. Each of the interference filters 90a through 90g transmits light having inherent wavelengths in accordance with the combination of the reagent contained in a chemical analysis slide 1 with the liquid sample, which is to be analyzed.

The light 92, which has passed through one of the interference filters 90a through 90g and which now has predetermined wavelengths, is guided by the optical fiber 89 and radiated out of one edge of the optical fiber 89 in the probe 41. The light 92 is then condensed by a condensing lens 98 and irradiated to a chemical analysis slide 1. Light 92R reflected by the chemical analysis slide 1 is condensed by a condensing lens 99 and received by a photodetector 94. The photodetector 94 detects the amount of the reflected light 92R and generates an output Q. The output Q is fed into a measurement circuit 95, which carries out processing, such as amplification and digitization, on the output Q and generates information about the amount of the reflected light 92R. For a single chemical analysis slide 1, the measurement of the amount of the reflected light is carried out at intervals of, for example, 10 to 15 seconds, and is finished within a predetermined time (e.g. 5 to 6 minutes).

The probe 41 also moves to the positions below a white reference plate 2a and a black reference plate 2b, which serve as reference density plates. Therefore, the measurement means 40 can also measure the amounts of light reflected by the white reference plate 2a and the black reference plate 2b. The amounts of the reflected light thus measured are used during the correction of values obtained from analyses. Also, when a chemical analysis slide 1 is conveyed by a slide pushing lever 52, which will be described later, from the slide stand-by section 15, the probe 41 moves to the position below a feed base 19, which will be described later. In this manner, the background density of the chemical analysis slide 1, i.e. the reflection density of the chemical analysis slide 1 to which no liquid sample has been applied, is found. A bar code reader 25 is located below part of the slide conveyance path between the slide stand-by section 15 and the feed base 19. When a chemical analysis slide 1 passes over this part of the slide conveyance path, the bar code reader 25 reads the bar code representing the kind of the reagent contained in the chemical analysis slide 1, the lot number of the chemical analysis slide 1, or the like, which bar code is recorded on a mount of the chemical analysis slide 1.

Figure 5:
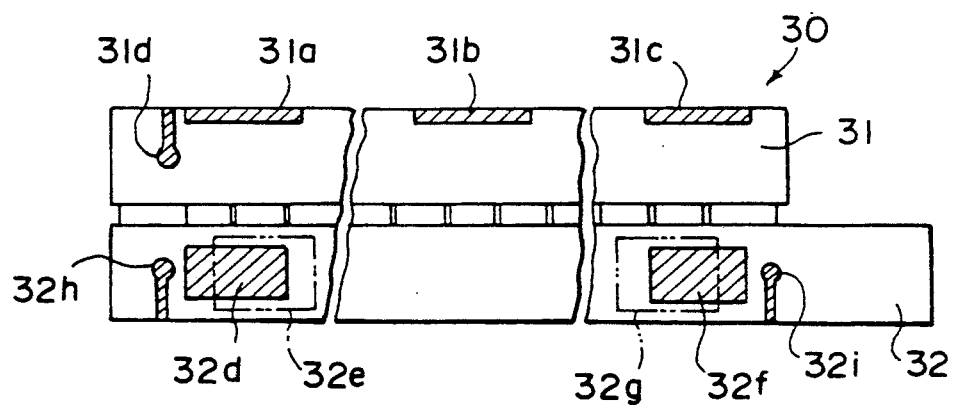
FIG. 5 is a front view showing an incubator.

FIG. 5 is a front view of the incubator 30 and shows how heaters for keeping the incubator 30 at a predetermined temperature are located. How the heaters are located will hereinbelow be described with reference to FIGS. 3, 4, and 5.

Heaters 32$d$, 32$e$, 32$f$, and 32$g$ are located in the vertical orientation in the vicinity of both edges of the lower member 32 of the incubator 30, which edges are taken in the transverse direction. The heaters 32$d$, 32$e$, 32$f$, and 32$g$ are located at the parts of the lower member 32, which extend downwardly with the groove 32$b$ shown in FIG. 4 intervening therebetween. A temperature sensor 32$h$ is located on the left side of the heater 32$d$. The left heaters 32$d$ and 32$e$ are controlled such that the temperature sensor 32$h$ indicates a predetermined temperature. A temperature sensor 32$i$ is located on the right side of the heater 32$f$. The right heaters 32$f$ and 32$g$ are controlled such that the temperature sensor 32$i$ indicates the predetermined temperature.

Heaters 31$a$, 31$b$, and 31$c$ are located in the horizontal orientation at the upper member 31 of the incubator 30. A temperature sensor 31$d$ is located on the left side of the heater 31$a$. The heaters 31$a$, 31$b$, and 31$c$ uniformly heat the incubator 30 from above and are controlled such that the temperature sensor 31$d$ indicates the predetermined temperature.

Figure 6:
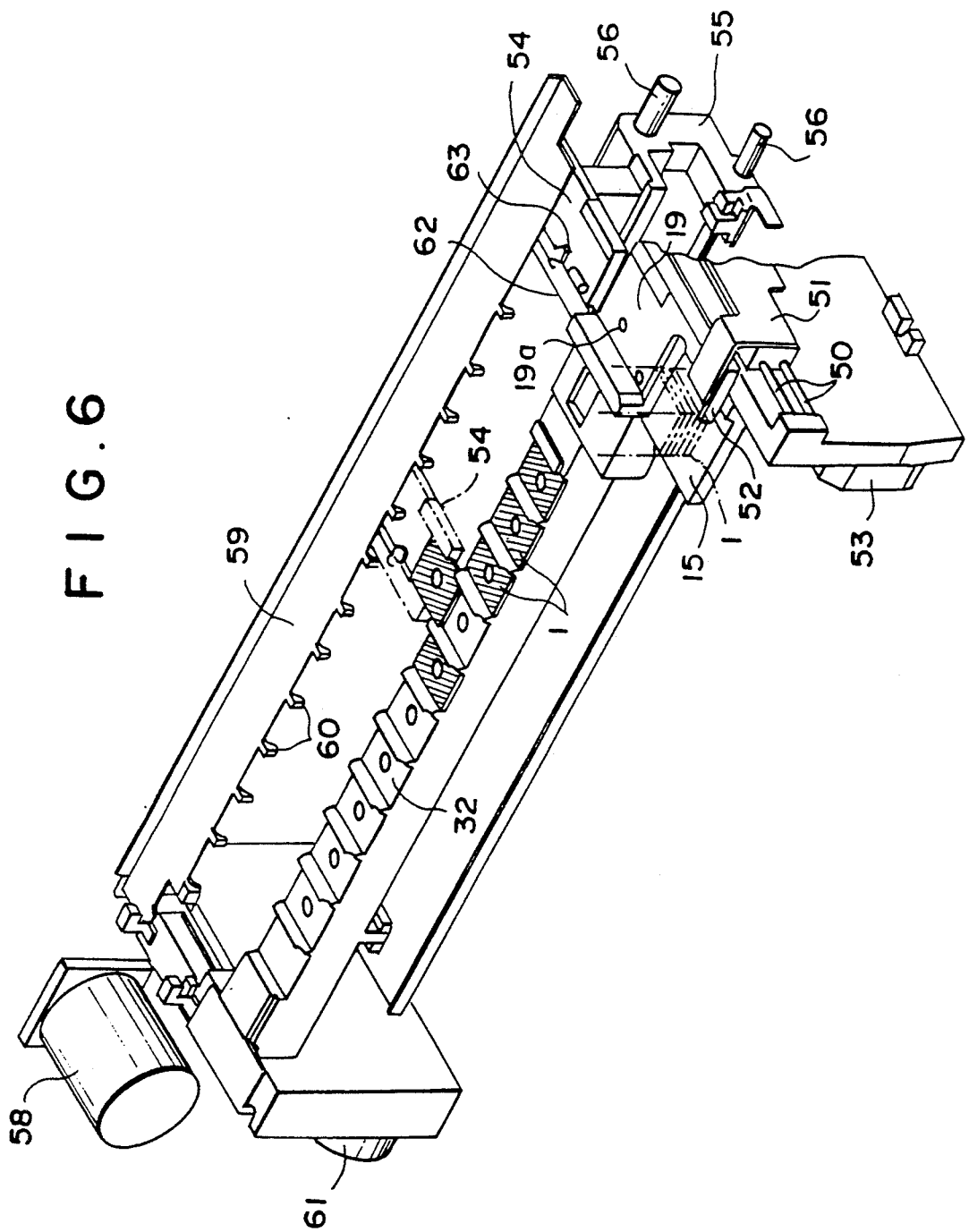
FIG. 6 is a perspective view showing a slide conveyance means of the biochemical analysis apparatus shown in FIG. 2.

The slide conveyance means will hereinbelow be described with reference to FIG. 6. Guide rods 50, 50 extend in the forward-backward direction. A block 51 is supported so that it can move along the guide rods 50, 50. The block 51 is provided with the slide pushing lever 52. The block 51 is moved forwardly and backwardly by a pushing lever operating motor 53. The feed base 19 is located at the rear of the slide stand-by section 15. A shuttle 54, which moves in the transverse direction, is located at the rear of the feed base 19. The shuttle 54 is secured to the upper part of a supporting base 55, which can move along guide rods 56, 56. Part of an endless wire 57 shown in FIG. 4 is secured to the supporting base 55. When the wire 57 is rotated by a shuttle operating motor 58, the supporting base 55 and the shuttle 54 are moved in the transverse direction. A slide feed-in bar 59 is supported above the shuttle 54 such that it can move forwardly and backwardly. Also, the slide feed-in bar 59 is provided with feed-in projections 60, 60, . . . at the positions facing the inlet openings of the compartments 33, 33, . . . of the incubator 30. The slide feed-in bar 59 is moved by a feed-in bar operating motor 61.

How the slide conveyance means operates will be described hereinbelow. First, the block 51 is located at the position shown in FIG. 6. At this time, the slide pushing lever 52 is located in front of the slide stand-by section 15. The pushing lever operating motor 53 is then activated, and the block 51 moves backwardly. The lowest chemical analysis slide 1 among the chemical analysis slides 1, 1, . . . , which are stacked in, for example, a cartridge at the slide stand-by section 15, is pushed by the slide pushing lever 52 onto the feed base 19. The feed base 19 has an opening 19$a$, through which the probe 41 irradiates light to the chemical analysis slide 1. In this manner, the background density of the chemical analysis slide 1 is found.

Thereafter, the sample application pipette 22 applies a predetermined amount of a liquid sample to the chemical analysis slide 1. The slide pushing lever 52 further moves backwardly and transfers the chemical analysis slide 1 onto the shuttle 54. The direction along which the pushing lever operating motor 53 rotates is thereafter reversed, and the block 51 returns to the position shown in FIG. 6. Before the block 51 thus returns, the slide pushing lever 52 rotates such that its leading edge faces backwardly. Therefore, when the block 51 returns, the slide pushing lever 52 does not move a chemical analysis slide 1 located in the slide stand-by section 15.

After the chemical analysis slide 1 is placed on the shuttle 54 in the manner described above, the shuttle operating motor 58 is activated to move the shuttle 54 to the position facing a predetermined compartment 33, into which the chemical analysis slide 1 is to be fed. Thereafter, the feed-in bar operating motor 61 is activated to move the slide feed-in bar 59 forwardly by a predetermined distance from the position shown in FIG. 6. As a result, the chemical analysis slide 1 on the shuttle 54 is pushed forwardly by a feed-in projection 60 of the slide feed-in bar 59. The chemical analysis slide 1 passes through the inlet opening of the corresponding compartment 33 and is accommodated in the compartment 33. At this time, if a chemical analysis slide 1, which has been used in the analysis, is present in the compartment 33, it will be pushed by the new chemical analysis slide 1 into the ejection box 80.

The chemical analysis slide 1, which has been accommodated in the compartment 33 in the manner described above, is incubated. The optical density of the chemical analysis slide 1, which depends on how much of a reaction product was formed by the reaction between the liquid sample and the reagent in the chemical analysis slide 1, is found with the probe 41.

In this example, one of the members, which guide the right and left edges of the chemical analysis slide 1 on the shuttle 54, serves as a slide ejection lever. Therefore, a chemical analysis slide 1, which has been accommodated in each compartment 33 during the last analysis among a series of analysis operations, can be discharged from the compartment 33 by the slide ejection lever. Specifically, a slide ejection lever 62 having a projection 63 on its inner surface is located on the shuttle 54 so that it can move forwardly and backwardly. The slide ejection lever 62 is urged backwardly by an urging means (not shown). When the last chemical analysis slide 1 is to be discharged from the compartment 33, the shuttle 54 is moved to a position at which the slide ejection lever 62 faces the middle part of the compartment 33. When the slide feed-in bar 59 moves forwardly in the manner described above, its feed-in projection 60 comes into contact with the projection 63 and pushes the slide ejection lever 62 forwardly. As a result, the slide ejection lever 62 moves forwardly against the urging force of the urging means and discharges the chemical analysis slide 1 from the compartment 33 into the ejection box 80.

In the manner described above, the measurement circuit 95 generates information about measured values S, W, and B representing the amounts of light reflected by the chemical analysis slide 1, the white reference plate 2$a$, and the black reference plate 2$b$. The information about the measured values S, W, and B is fed into an operation means 65. The operation means 65 calculates the reflection density OD of the chemical analysis slide 1 from the measured values S, W, and B. The calculation is carried out with the formula $$OD = \log\left(\frac{W - B}{10^{-OD_w}(S - B) - 10^{-OD_b}(S - W)}\right)$$

where W denotes the measured value representing the amount of light reflected by the white reference plate $2a$, B denotes the measured value representing the amount of light reflected by the black reference plate $2b$, S denotes the measured value representing the amount of light reflected by the chemical analysis slide 1, $OD_w$ denotes the reflection density of the white reference plate $2a$ determined with a reference density meter, and $OD_b$ denotes the reflection density of the black reference plate $2b$ determined with a reference density meter.

From a plurality of the reflection densities OD, which have been found in the manner described above, a calculation is made to find the optical density at the time when, for example, a predetermined analysis time has occurred after the liquid sample was applied to the chemical analysis slide 1. From the optical density thus found, the concentration D of the specific constituent is determined.

The operation means 65 feeds a signal, which represents the concentration D thus determined, to a control means 66 shown in FIGS. 3 and 4. The control means 66 works to display the information about the concentration represented by the signal on the display section 13, and to print the information about the concentration on the recording sheet 12A by a printer (not shown). The recording sheet 12A is discharged from the ejection opening 12 shown in FIG. 2.

FIG. 1 is a flow chart showing how the information about the measured values representing the amounts of light reflected by a reference density plate is processed in the embodiment of the method for detecting defects in a measurement means of a biochemical analysis apparatus in accordance with the present invention. The processing will hereinbelow be described with reference to FIGS. 1 and 7. The processing is begun in a step P1. In a step P2, the movement mechanism for the probe 41, or the like, is set to the initial condition. Thereafter, in a step P3, light is irradiated to the white reference plate $2a$, and the amount of light reflected thereby is measured. At this time, the gain of the measurement circuit 95 shown in FIG. 7 is set to 1. Also, the filter plate 90 is rotated, and the light $92a$ is selectively passed through one of the interference filters $90a$ through $90g$. The light 92, which has passed through one of the interference filters $90a$ through $90g$, is irradiated to the white reference plate $2a$. This operation is repeated for all of the interference filters $90a$ through $90g$. In this manner, the amounts of light 92R reflected by the white reference plate $2a$ are measured sequentially. The voltage outputs generated by the photodetector 94 are digitized, and the signals which are thus obtained and which represent the measured values Xa, Xb, Xc, Xd, Xe, Xf, and Xg are stored in an internal memory of the control means 66.

Thereafter, in a step P4, one of the measured values Xa through Xg, e.g. the measured value Xa, is compared with a predetermined threshold value C1. In cases where C1>Xa, it is judged that the amount of light produced by the light source $18a$ is insufficient, and a "defective lamp" warning is issued in a step P5. By way of example, the warning is issued with the recording sheet 12A. Also, in a step P6, the whole measurement means stops.

In cases where it is judged in the step P4 that C1≦Xa, the measured value Xa is compared with a threshold value C2, which is larger than the threshold value C1, in a step P7. In cases where C2>Xa, it is judged that the service life of the light source $18a$ has run out, and a "lamp replacement" message is issued in a step P8. The message is displayed at the display section 13.

In cases where C2≦Xa, it is judged that the light source $18a$ is normal. In a step P9, the ratio (Xb/Xa) of the measured value Xb to the measured value Xa is compared with a value of 0.9E1 and a value of 1.1E1, where E1 denotes the value of Xb/Xa obtained when both the interference filters $90a$ and $90b$ are normal. In cases where 0.9E1<Xb/Xa<1.1E1, i.e. in cases where the value of Xb/Xa falls within the range of ±10% of E1, it is judged that both the measured values Xa and Xb are normal. This is because the probability that both the interference filters $90a$ and $90b$ will deteriorate simultaneously is very low. In cases where 0.9E1<Xb/Xa<1.1E1, a judgment is then made as to whether 0.9E2<Xc/Xa<1.1E2. In cases where 0.9E2<Xc/Xa<1.1E2, a judgment is then made as to whether 0.9E3<Xd/Xa<1.1E3. In the same manner, judgments are made sequentially. Finally, the judgment is made as to whether 0.9E6<Xg/Xa<1.1E6. Like E1, E2 denotes the value of Xc/Xa obtained when both the interference filters $90a$ and $90c$ are normal. This also applies to E3 through E6. In FIG. 1, the judgment is made in a step P10 as to whether 0.9E6<Xg/Xa<1.1E6. Between the step P9 and the step P10, four similar judgments are carried out.

In cases where the inequality is not satisfied even in one of the six judgments, a "defective filter" message is issued in a step P11. Also, in a step P12, the whole measurement means stops. This message is given, for example, on the recording sheet 12A. The message also indicates which interference filter has been judged to be defective. Specifically, in cases where the inequality expressed as 0.9E1<Xb/Xa<1.1E1 is not satisfied, the interference filter $90b$ is indicated as being defective. In cases where the inequality expressed as 0.9E3<Xd/Xa<1.1E3 is not satisfied, the interference filter $90d$ is indicated as being defective. In cases where none of the six inequalities described above is satisfied, the interference filter $90a$ is indicated as being defective. For the reasons described above, defects of the interference filters $90a$ through $90g$ can be detected.

In cases where all of the six inequalities are satisfied, in a step P13, the gain of the measurement circuit 95 is set automatically. Thereafter, in a step P14, light is irradiated through each of the interference filters $90a$ through $90g$ to the white reference plate $2a$, and the amount of light reflected by the white reference plate $2a$ is measured. Thereafter, a judgment is made as to whether each of measured values Xa' through Xg' thus obtained falls within the range of a predetermined lower limit value G1 to a predetermined upper limit value G2. In cases where even one of the measured values Xa' through Xg' is smaller than the lower limit value G1 or is larger than the upper limit value G2, in a step P16, a "gain setting error" message is issued with, for example, the recording sheet 12A. Also, in a step P17, the measurement means stops. In cases where all of the measured values Xa' through Xg' fall within this range, it is judged that all of the elements of the measurement means are normal. Also, in a step P18, measurements of reflection densities of the chemical analysis slides 1, 1, . . . are carried out. The lower limit value G1 and the upper limit value G2 may vary for each of the interference filters 90a through 90g.

Also, after the measurements of reflection densities of the chemical analysis slides 1, 1, . . . are begun, in a step P19, the measurement of the amount of light reflected by the white reference plate 2a is carried out at predetermined time intervals. Specifically, each time the probe 41 once moves along a plurality of the chemical analysis slides 1, 1, . . . , which are accommodated in the compartments 33, 33, . . . , and returns, the probe 41 is operated to measure the amounts of light reflected by the white reference plate 2a and the black reference plate 2b, which amounts are used during the correction of the results of analyses. At this time, after the probe 41 first returns to the position facing the white reference plate 2a, the light 92 which has passed through the interference filter 90a is irradiated to the white reference plate 2a, and the amount of the light 92R reflected by the white reference plate 2a is measured. This operation is also carried out for the interference filters 90b and 90c. Thereafter, the probe 41 again moves along the plurality of the chemical analysis slides 1, 1, . . . , which are accommodated in the compartments 33, 33, . . . , and returns to the position facing the white reference plate 2a. At this time, the aforesaid operation is repeated for the interference filters 90d, 90e, and 90f. After the probe 41 then moves along the plurality of the chemical analysis slides 1, 1, . . . , which are accommodated in the compartments 33, 33, . . . , and returns to the position facing the white reference plate 2a, the aforesaid operation is repeated for the interference filter 90g. By way of example, in cases where it takes 13 seconds for the probe 41 to reciprocate once, the aforesaid operation for each interference filter is carried out once per approximately 39 seconds.

In a step P20, a measured value Xn, which is obtained in the manner described above during the n'Th measurement for each interference filter, is compared with a measured value Xn−1, which was obtained in the previous measurement for the interference filter. A judgment is made as to whether the absolute value of the difference between the measured values Xn and Xn−1 is not larger than a predetermined threshold value H. In cases where the absolute value of the difference between the measured values Xn and Xn−1 is not larger than the predetermined threshold value H, it is judged that no deviation in position of the elements of the measurement means occurs between when the previous measurement was carried out and when the current measurement is carried out. Therefore, in such cases, in a step P23, the information about the measured values obtained for the chemical analysis slides 1, 1, . . . is output as being correct values. Thereafter, the analysis are finished in a step P24. In cases where the absolute value of the difference between the measured values Xn and Xn−1 is larger than the predetermined threshold value H, it is judged that a failure occurred with the interference filter. In such cases, in a step P21, a judgment is made as to whether it is the first problem to occur during the current measurement. In cases where it is the first problem to occur during the current measurement, the processing returns to the step P2. In the step P2, the movement mechanism is initially set, and the aforesaid processing is repeated. In cases where it is not the first problem to occur during the current measurement, in a step P22, a "defective measurement" message is issued. By way of example, the message is issued with the recording sheet 12A. When the message is issued, it can be regarded that the concentration D determined in the manner described above is not reliable.

The processes in the steps P19 through P22 need not necessarily be carried out. However, the processes in the steps P19 through P22 should preferably be carried out because the operator of the biochemical analysis apparatus can find a deviation in position of the elements of the measurement means during the operation of the biochemical analysis apparatus.

The method for detecting defects in a measurement means of a biochemical analysis apparatus in accordance with the present invention is applicable also when test films are utilized in biochemical analysis apparatuses.

I claim:

1. A method for detecting defects in a measurement means of a biochemical analysis apparatus wherein a droplet of liquid sample is applied to an analysis medium containing a reagent, which chemically reacts with a specific constituent in the liquid sample, the analysis medium is then incubated, the optical densities of the analysis medium are determined, and concentrations of the specific constituent in the liquid sample are determined from the optical densities of the analysis medium thus determined, the method for detecting defects in the measurement means of the biochemical analysis apparatus comprising the steps of:
(a) irradiating light, which has passed through a plurality of interference filters by turns, to a reference density plate at predetermined time intervals,
(b) measuring amounts of light reflected by said reference density plate,
(c) comparing a set of the amounts of light reflected, which have thus been measured, with one another, and
(d) detecting defects in the measurement means from the results of the comparison.

2. A method as defined in claim 1 wherein the defects in said measurement means are defects in said interference filters.

3. A method as defined in claim 1 wherein the defects in said measurement means are defects in a light source.

4. A method as defined in claim 1 wherein the defects in said measurement means are deviations in position of elements of said measurement means.

5. A method as defined in claim 1 wherein said reference density plate is a white reference plate.

6. A method as defined in claim 1 wherein the analysis medium is a chemical analysis slide.

7. A method as defined in claim 1 wherein the analysis medium is a long test film.

8. A method as defined in claim 1 wherein the optical densities of the analysis medium are determined by use of the formula $$OD = \log\left(\frac{W - B}{10^{-OD_w}(S - B) - 10^{-OD_b}(S - W)}\right)$$

where W denotes the measured value representing the amount of light reflected by a white reference plate, B denotes the measured value representing the amount of light reflected by a black reference plate, S denotes the measured value representing the amount of light reflected by the analysis medium, ODw denotes the reflection density of the white reference plate determined with a reference density meter, and ODb denotes the reflection density of the black reference plate determined with a reference density meter.

9. A method for detecting defects in a biochemical analysis apparatus, the biochemical analysis apparatus includes an analysis medium containing a reagent, the analysis medium receives a liquid sample, the biochemical analysis apparatus determines optical densities of the analysis medium and determines concentrations of specific constituents in the liquid sample, said method comprising the steps of:

(a) sequentially irradiating light through a plurality of interference filters to a white reference plate;

(b) respectively measuring reflected amounts of light from the white reference plate for each of the plurality of interference filters; and (c) detecting a defect in at least one of the plurality of interference filters by comparing ratios of the reflected amounts obtained in step (b) with predetermined normal ratios of reflected amounts.

10. A method as defined in claim 9 wherein the biochemical analysis apparatus includes a filter plate and light source, the filter plate comprises the plurality of interference filters, and wherein said method further comprises the step of (d) detecting a defect in the light source by comparing one of the reflected amounts of light with a predetermined threshold value.

11. A method as defined in claim 10 wherein step (a) comprises the step of (a1) rotating the filter plate with respect to the light source to irradiate light through each of the plurality of interference filters.

12. A method as defined in claim 10 wherein said method further comprises the steps of:

(e) setting a reflected light gain for the biochemical analysis apparatus;

(f) irradiating light through one of the interference filters to the white reference plate;

(g) measuring an amount of reflected light from the white reference plate; and (h) detecting a gain error in the biochemical analysis apparatus by comparing the amount of the reflected light measured in step (g) with predetermined upper and lower limits on the amount of reflected light.

13. A method as defined in claim 9 wherein said method further comprises the steps of:

(e) setting a reflected light gain for the biochemical analysis apparatus;

(f) irradiating light through one of the interference filters to the white reference plate;

(g) measuring an amount of reflected light from the white reference plate; and (h) detecting a gain error in the biochemical analysis apparatus by comparing the amount of the reflected light measured in step (g) with predetermined upper and lower limits on the amount of the reflected light.

* * * * *